(12) United States Patent
Spivey et al.

(10) Patent No.: US 10,182,808 B2
(45) Date of Patent: Jan. 22, 2019

(54) KNOTLESS SUTURE ANCHOR GUIDE

(71) Applicant: DePuy Synthes Products, Inc., New Brunswick, NJ (US)

(72) Inventors: James T. Spivey, Whitehouse Station, NJ (US); Ami S. Joshi, East Providence, RI (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 282 days.

(21) Appl. No.: 14/694,526

(22) Filed: Apr. 23, 2015

(65) Prior Publication Data

US 2016/0310125 A1     Oct. 27, 2016

(51) Int. Cl.
*A61B 17/04* (2006.01)
*A61B 17/17* (2006.01)

(52) U.S. Cl.
CPC .......... *A61B 17/0401* (2013.01); *A61B 17/17* (2013.01); *A61B 17/0483* (2013.01); *A61B 2017/0409* (2013.01); *A61B 2017/0412* (2013.01); *A61B 2017/0414* (2013.01); *A61B 2017/0445* (2013.01); *A61B 2017/0464* (2013.01)

(58) Field of Classification Search
CPC . A61B 17/04; A61B 17/0401; A61B 17/0469; A61B 2017/0409
See application file for complete search history.

(56) References Cited

U.S. PATENT DOCUMENTS

| | | |
|---|---|---|
| 2,919,692 A | 1/1960 | Wolfgang |
| 4,632,100 A | 12/1986 | Somers et al. |
| 5,250,055 A | 10/1993 | Moore et al. |
| 5,312,391 A | 5/1994 | Wilk |
| RE34,762 E | 10/1994 | Goble et al. |
| 5,458,604 A | 10/1995 | Schmieding |
| 5,562,684 A | 10/1996 | Kammerer |
| 5,573,548 A * | 11/1996 | Nazre ................ A61B 17/0401 606/232 |
| 5,662,654 A | 9/1997 | Thompson |
| 5,762,629 A | 6/1998 | Kambin |
| 5,792,044 A | 8/1998 | Foley et al. |

(Continued)

FOREIGN PATENT DOCUMENTS

| | | |
|---|---|---|
| EP | 2749230 A2 | 7/2014 |
| WO | 2006009471 A1 | 1/2006 |
| WO | 2009023034 A1 | 2/2009 |

OTHER PUBLICATIONS

European Search Report for EP Application No. 16166725.8, dated Aug. 16, 2016. (9 pages).

*Primary Examiner* — Diane Yabut

(57) ABSTRACT

Devices and methods are provided for forming a hole in bone and implanting a suture anchor in the bone hole. The devices and methods disclosed herein allow a suture coupled to tissue to be passed through a shaft that is also configured to receive a drill bit. Exemplary guide devices are provided having a shaft with a cross-sectional shape that allows the suture to be seated in a secondary region that is offset from a primary region that receives the drill bit therethrough. A drill bit can be passed through the shaft without causing any damage to the suture extending through the shaft, and subsequently an anchor can be advanced along the suture through the shaft and guided into the bone hole.

19 Claims, 15 Drawing Sheets

(56) References Cited

U.S. PATENT DOCUMENTS

| | | |
|---|---|---|
| 5,824,011 A | 10/1998 | Stone et al. |
| RE36,020 E | 12/1998 | Moore et al. |
| 6,007,487 A | 12/1999 | Foley et al. |
| 6,013,083 A | 1/2000 | Bennett |
| 6,152,871 A | 11/2000 | Foley et al. |
| 6,176,823 B1 | 1/2001 | Foley et al. |
| 6,206,886 B1 | 3/2001 | Bennett |
| 6,325,804 B1 | 12/2001 | Wenstrom, Jr. et al. |
| 6,425,859 B1 | 7/2002 | Foley et al. |
| 6,520,907 B1 | 2/2003 | Foley et al. |
| 8,197,482 B2 | 6/2012 | Stone |
| 8,361,079 B2 | 1/2013 | Pandya |
| 8,403,963 B2 | 3/2013 | Garcia-Bengochea et al. |
| 8,579,974 B2 | 11/2013 | Pandya |
| 8,617,176 B2 | 12/2013 | Lizardi et al. |
| 8,790,352 B2 | 7/2014 | Smith et al. |
| 2005/0288682 A1* | 12/2005 | Howe ................ A61B 17/0401 606/104 |
| 2006/0030872 A1 | 2/2006 | Culbert et al. |
| 2007/0112352 A1 | 5/2007 | Sorensen et al. |
| 2008/0058816 A1* | 3/2008 | Philippon .......... A61B 17/0401 606/326 |
| 2008/0287981 A1 | 11/2008 | Culbert et al. |
| 2010/0049201 A1 | 2/2010 | Re |
| 2012/0123473 A1 | 5/2012 | Hernandez |
| 2012/0209279 A1 | 8/2012 | Snyder et al. |
| 2013/0085528 A1 | 4/2013 | DiMatteo et al. |
| 2013/0158596 A1 | 6/2013 | Miller et al. |
| 2013/0253647 A1 | 9/2013 | Saliman et al. |
| 2014/0107657 A1 | 4/2014 | Norton et al. |
| 2015/0342594 A1* | 12/2015 | Stone ................ A61B 17/0401 606/232 |

\* cited by examiner

KNOTLESS SUTURE ANCHOR GUIDE

FIELD OF THE INVENTION

The present invention relates to knotless suture anchor guide devices and methods.

BACKGROUND OF THE INVENTION

When soft tissue tears away from bone, reattachment becomes necessary. Various devices, including sutures, screws, staples, wedges, anchors and plugs have been used in the prior art to secure soft tissue to bone. In ball-and-socket joints, such as the shoulder or hip, reattachment is often necessary due to the high stress and movement demanded of the ball-and-socket bone structures. Often, such procedures involve surgical reattachment of labral tissue. The labral tissue, or labrum, is a type of soft tissue or cartilage that surrounds the socket of ball-and-socket joints, such as the shoulder and the hip joint. The labrum forms a ring around the edge of the bony socket of the joint, and helps to provide stability to the joint, yet unlike bone, it also allows flexibility and motion.

Current procedures can involve the use of a knotless suture anchor for reattaching the labrum to the bone, as knotless anchors avoid the need to tie a knot in a constricted space, such as a ball-and-socket joint. A suture is first passed through the tissue to be reattached, and the trailing ends of the suture extending outside of the patient are then loaded onto the anchor. A drill guide is typically passed through the tissue and positioned in alignment with the anchor site, and a drill bit is passed through the drill guide to form a hole in the bone. The suture is positioned off to the side while the hole is being formed. Once the bone hole is prepared, the drill guide is removed and the anchor can be inserted into the bone hole using an inserter tool. The suture is tensioned during advancement of the anchor so as to pull the tissue toward the bone hole, thereby anchoring the tissue to the bone.

While knotless anchors can be very effective in reattaching soft tissue to bone, the small size of the anchor and the tight constraints of the ball-and-socket joint can make it difficult to locate the bone hole and to insert the anchor into the bone hole. In the shoulder joint, for example, the humeral head will typically return to its resting position within the socket after the drill guide is removed, obstructing the path to the hole. In the hip, visualization of the hole can be a challenge due to challenging angles and the tight nature of the joint space.

Accordingly, there is a need for improved methods and devices for guiding an anchor, such as a knotless suture anchor, into a bone hole.

SUMMARY OF THE INVENTION

Various devices and methods are provided for facilitating the implantation of a knotless suture anchor in a bone hole to reattach tissue to bone. In one embodiment, a knotless suture anchor guide device is provided and includes a handle and a shaft extending distally from the handle. The shaft can have an inner lumen with a cross-sectional shape that includes a primary region configured to receive a drill bit therethrough, and an offset region configured to seat a length of suture such that the suture seats outside of the primary region and therefore does not come into contact with a cutting portion of the drill bit.

The handle can have a variety of configurations and can include various features. In one embodiment, the handle can have a generally elongate cylindrical shape with an inner lumen extending therethrough. The inner lumen in the handle can be co-axial with the inner lumen of the shaft. The handle can in other aspects extend at a non-zero angle relative to the shaft. In another embodiment, the handle or the shaft can include a suture-engaging feature for engaging a suture extending through the inner lumen. In one embodiment, the suture-engaging feature can be in the form of a slit for releasably engaging a suture. The handle can include other features such as an irrigation hole formed therein and in communication with the inner lumen of the shaft such that irrigation fluid can flow through the shaft and exit through the irrigation hole. In another embodiment, the handle can include a side arm coupled thereto and having a channel configured to seat an elongate tool therein.

The shaft can also have a variety of configurations and can include various features. In one embodiment, the shaft can include a distal end with a relief cut-out formed therein for seating a suture extending through the inner lumen. The relief cut-out and the suture-engaging feature can be longitudinally aligned with the offset region. In one exemplary embodiment, the relief cut-out in the distal end of the shaft can be substantially U-shaped and can include at least one notch formed in a proximal end thereof. The offset portion of the shaft can also have various configurations, and it can have various shapes, such as substantially triangular, substantially circular, or substantially semi-circular.

In another embodiment, a suture anchor and delivery kit is provided and includes a delivery tool having a handle with an elongate shaft extending distally therefrom. The shaft has an inner lumen extending therethrough, and the inner lumen has a cross-section with a primary region for receiving a drill bit and a secondary offset region. The kit also includes a suture anchor assembly having an anchor configured to be implanted in bone, and a suture configured to be coupled to the anchor. The suture is configured to extend through the inner lumen in the shaft and to sit within the secondary offset region such that a drill bit can be passed through the primary region of the inner lumen in the shaft without contacting the suture.

The delivery tool can have a variety of configurations. In one embodiment, the handle has an inner lumen extending therethrough and in communication with the inner lumen in the shaft. The handle or the shaft can include features such as a suture-engaging feature formed therein and configured to releasably engage the suture, and/or an irrigation hole formed therein and configured to allow irrigation fluid to flow through the inner lumen in the shaft and to exit through the irrigation hole. The shaft can also have various features and can include, for example, a relief cut-out formed in a distal end thereof and longitudinally aligned with the secondary offset region of the inner lumen. The distal end of the shaft can include other features such as a viewing window formed therein, and/or bone engaging teeth formed thereon.

In other aspects, a method for anchoring tissue to bone is provided and includes passing a suture through tissue to be anchor to bone, and passing a trailing end of the suture extending from the tissue through an inner lumen in an elongate shaft of a delivery tool. The method also includes positioning a distal end of the elongate shaft adjacent to bone, and advancing a drill bit through the inner lumen of the shaft and into the bone to form a hole in the bone. The suture extending through the inner lumen can be offset from the path of the drill bit such that the drill bit does not contact the suture. The method further includes advancing an anchor along the suture and through the inner lumen of the guide tool to deliver the anchor into the bone hole.

While the method can vary, in one embodiment passing a trailing end of the suture through the inner lumen of the elongate shaft includes seating a portion of the suture within a relief cut-out formed in a distal end of the shaft, and seating a portion of the suture within a suture-engaging feature of the delivery tool such that the suture is tensioned between the relief cut-out and the suture-engaging feature. In other aspects, positioning a distal end of the elongate shaft adjacent to bone includes positioning teeth formed on a distal end of the shaft into engagement with the bone. The method can also include viewing at least one of the drill bit, the suture, and the anchor through a viewing window formed in a distal portion of the elongate shaft. In another embodiment, prior to advancing the anchor, the anchor can be coupled to a portion of the suture extending proximally from the delivery tool, and advancing the anchor can include coupling the anchor to an inserter tool and passing the inserter tool with the anchor coupled thereto through the inner lumen of the shaft. Tension can be applied to the suture while the anchor is advanced along the suture through the inner lumen of the shaft.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
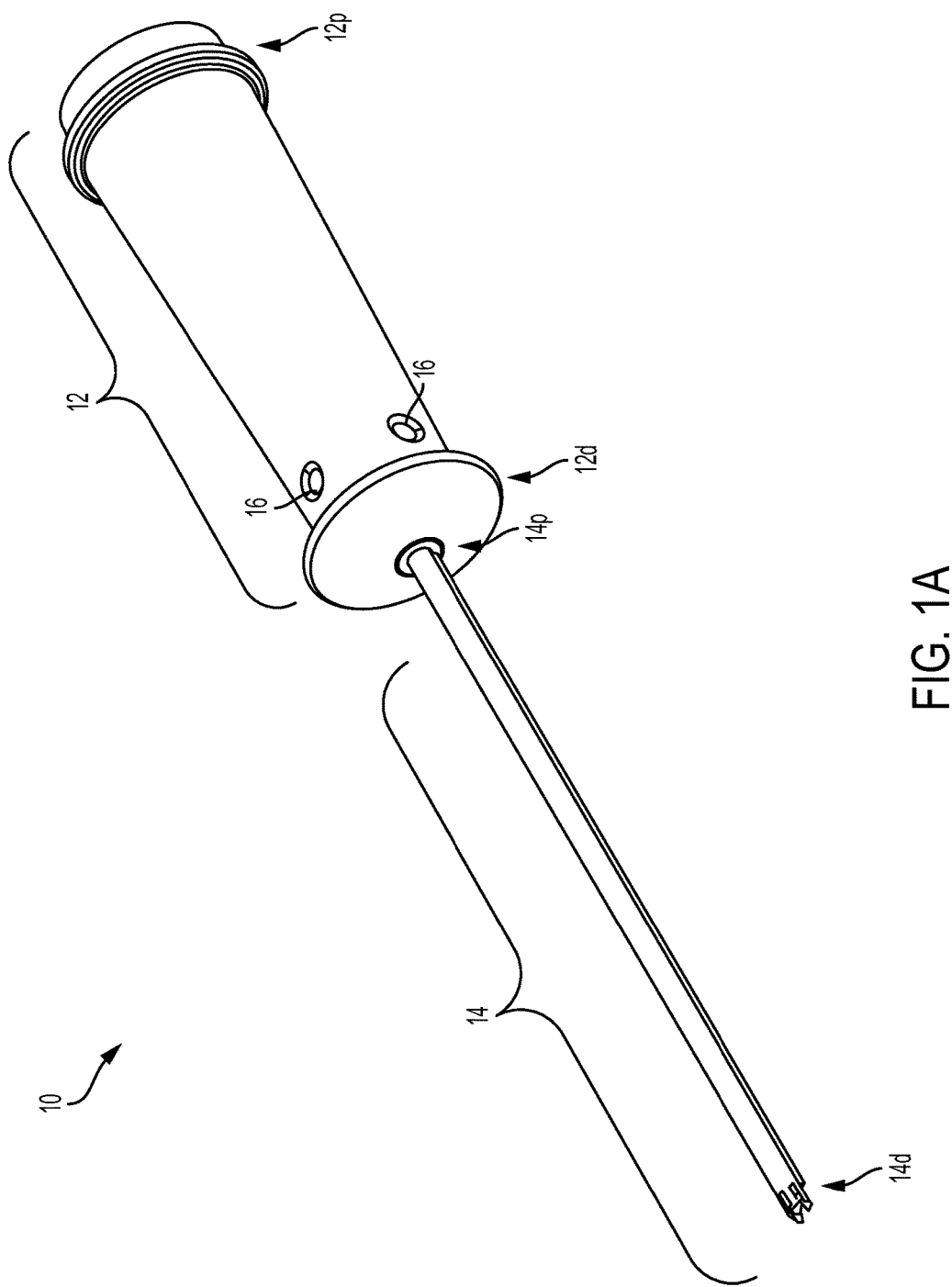
FIG. 1A is a perspective view of one embodiment of a guide device having a handle and an elongate shaft that are coaxial.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various devices and methods are provided for guiding a drill bit through tissue to form a hole in bone, and for guiding a suture anchor into the bone hole. The devices and methods disclosed herein are particularly advantageous as they allow a suture coupled to tissue to be passed through a shaft that is also configured to receive a drill bit. The shaft has a cross-sectional shape that allows the suture to be seated in a secondary region that is offset from a primary region that receives the drill bit therethrough. In this way, a suture mated at one end to tissue can extend through the entire length of the shaft, and a drill bit can be passed through the shaft for forming a bone hole in bone without causing any damage to the suture. With the drill bit removed, an anchor can be advanced along the suture and guided by the guide into the bone hole formed by the drill bit. By allowing the suture to pass through the shaft of the guide device, the guide device can guide the anchor directly into the bone hole. This may avoid the deficiencies of the prior art techniques discussed above. By allowing the suture to pass through the guide device, additional steps may also be eliminated thereby simplifying and shortening the procedure.

Various embodiments of guide devices are disclosed herein. In general, FIGS. 1A-1E illustrate one embodiment of a guide device 10 having a handle 12 and an elongate shaft 14 extending from the handle. In this embodiment, the handle 12 and the elongate shaft 14 are longitudinally aligned and have coaxial lumens extending therethrough. FIGS. 2A-2C illustrate another embodiment of a guide device 100 having a handle 112 and an elongate shaft 114 extending from the handle. In this embodiment, the handle 112 extends at an angle, e.g., a non-zero angle, relative to the elongate shaft 114. Such a configuration may be advantageous for difficult to access anatomies, such as the hip joint.

Figure 3A:
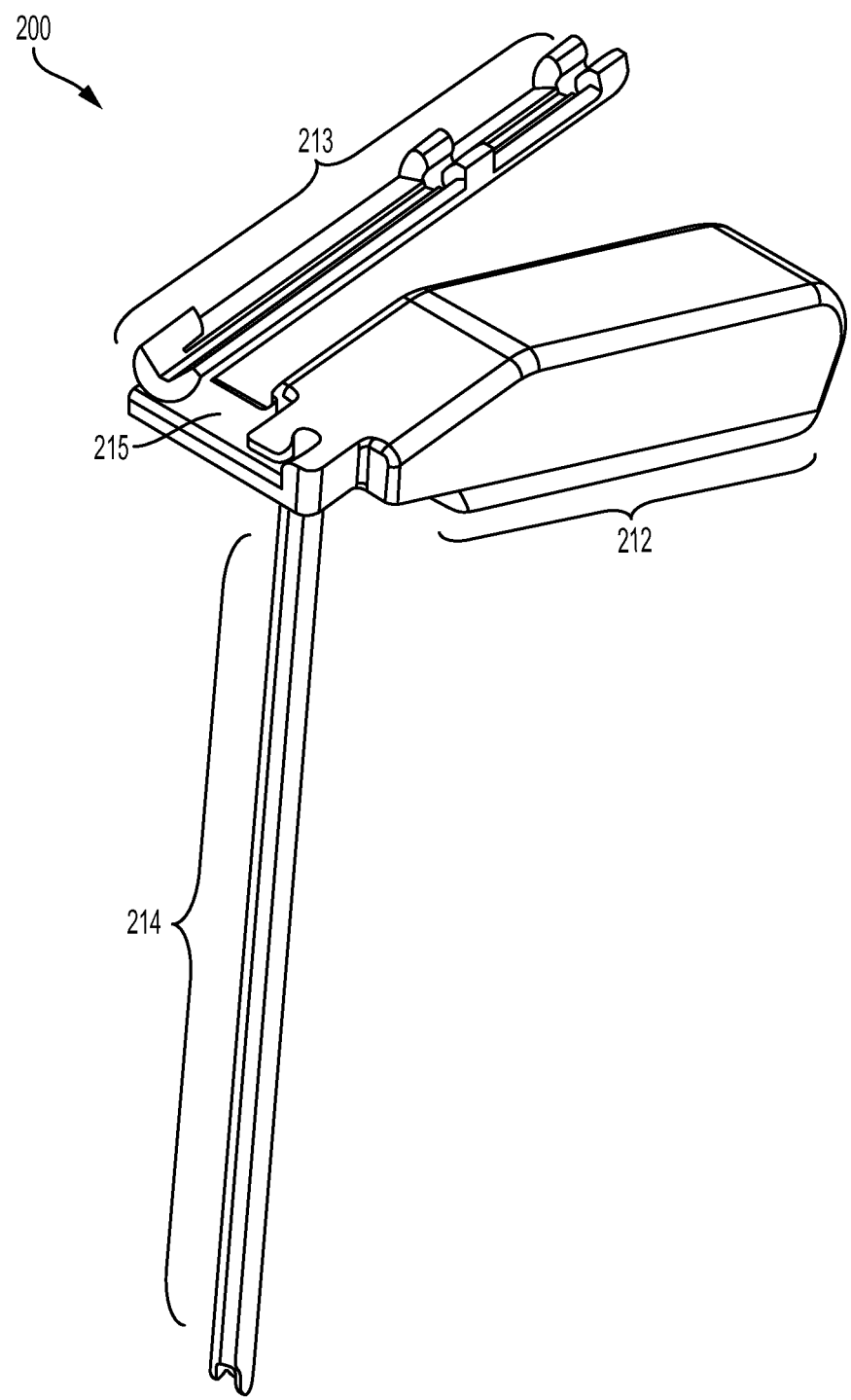
FIG. 3A is a perspective view of another embodiment of a guide device having a handle with a side support coupled thereto, and having an elongate shaft that extends from the handle.
Figure 3B:
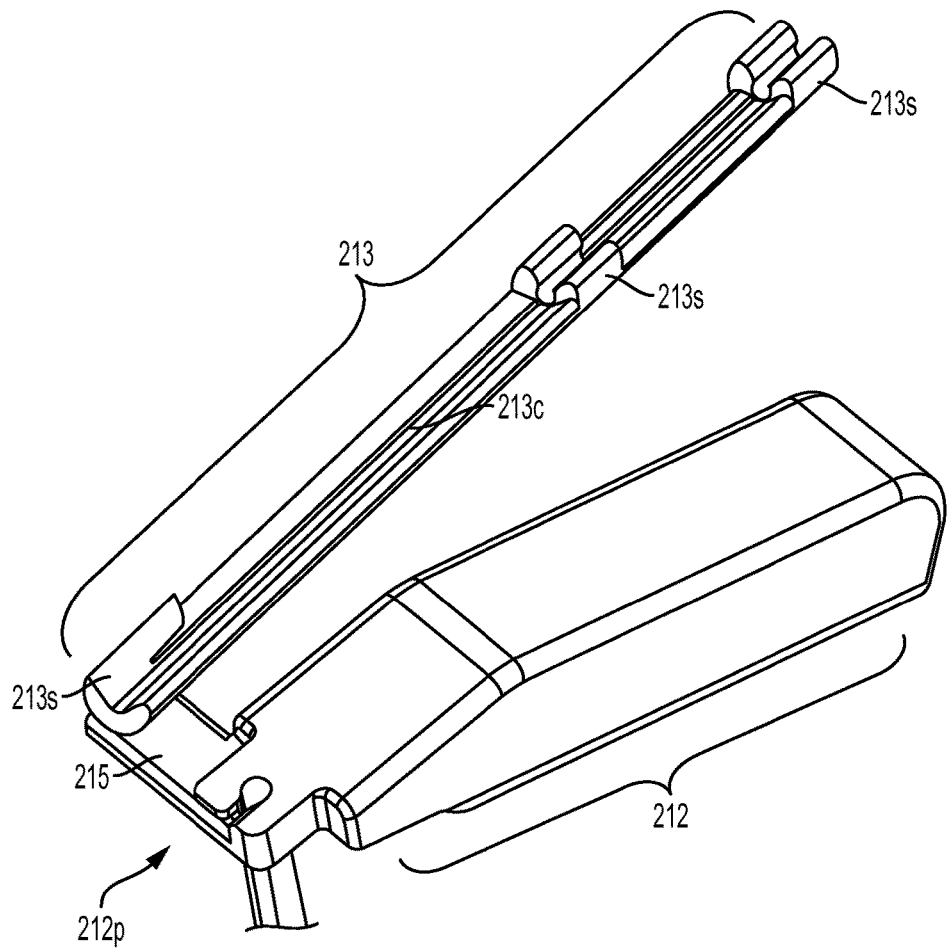
FIG. 3B is a top perspective view of the handle and side support of the device of FIG. 3A.

FIGS. 3A-3B illustrate yet another embodiment of a guide device 200 having a handle 212 and an elongate shaft 214 extending therefrom. In this embodiment, the handle includes a support arm 213 coupled thereto and configured to seat a tool for inserting the anchor through the shaft. A person skilled in the art will appreciate that the various features on each of the disclosed embodiments can be used in any combination and in connection with any of the disclosed guide devices.

Figure 1B:
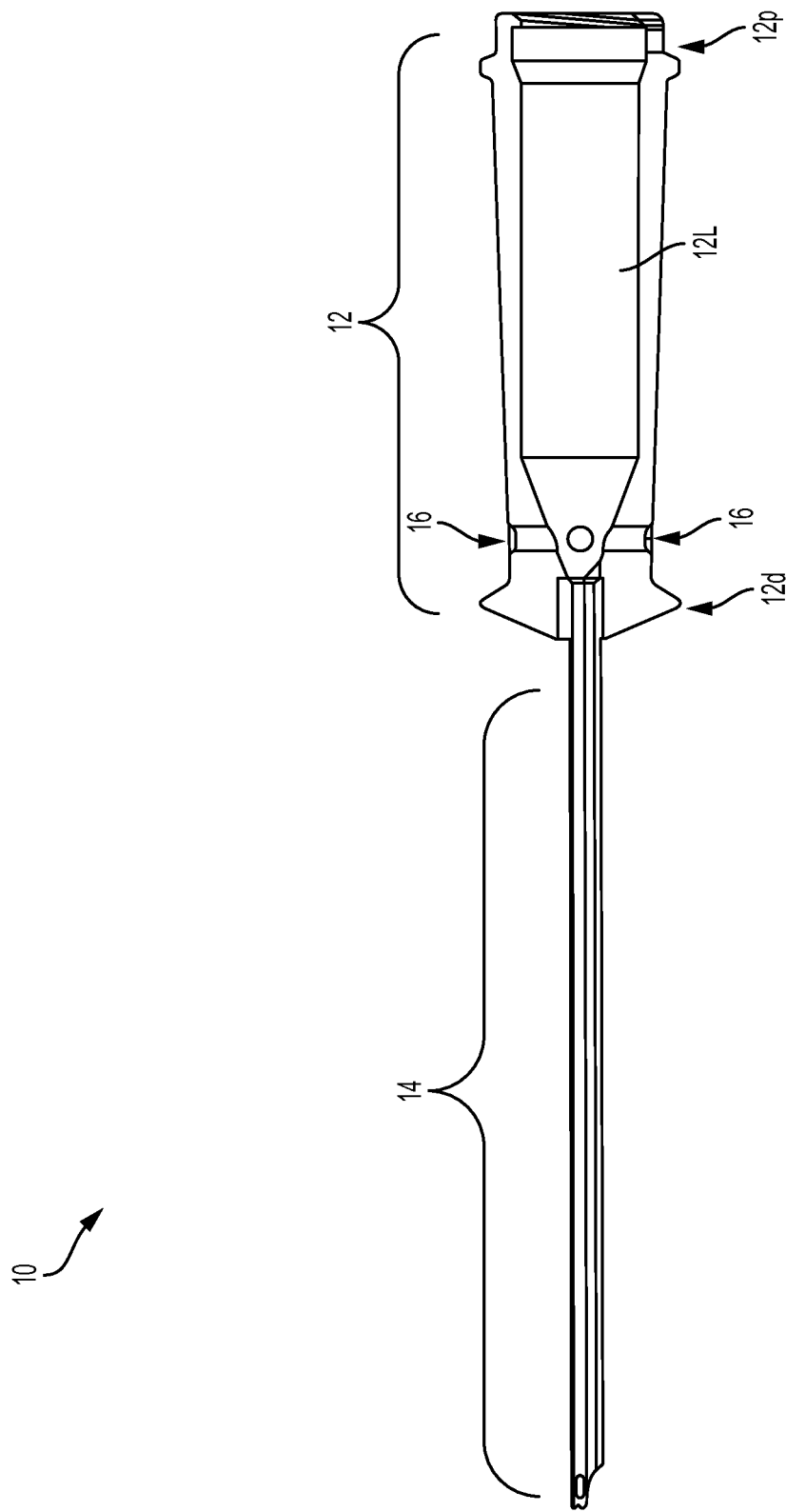
FIG. 1B is a cross-sectional view of the guide device of FIG. 1A.

Turning first to the embodiment of FIGS. 1A-1E, as indicated above the guide device 10 has a handle 12 with a proximal end 12p and a distal end 12d. The handle can have various shapes and sizes, and as shown has a generally elongate cylindrical shape to facilitate grasping. The illustrated handle 12 has an inner lumen 12i extending therethrough between the proximal end distal ends 12p, 12d thereof. The illustrated inner lumen 12i has a constant diameter, however it can vary in diameter along its length. As shown in FIG. 1B, the inner lumen 12i is substantially constant in diameter from the proximal end 12p toward the distal end 12d along a substantial portion of the handle 12. However, the inner lumen 12i tapered radially inward near the distal end 12d. The tapered configuration may facilitate positioning of a suture extending through from the shaft 14 into the inner lumen of the handle 12, as will be discussed in more detail below.

As further shown in FIGS. 1A-1B, the handle 12 also includes several irrigation holes 16 formed therein and extending through a sidewall thereof. The irrigation holes 16 extend into the inner lumen 12i such that fluid flowing through the inner lumen 12i, e.g., from the shaft 14, can exit out through the irrigation holes 16. Since saline is often delivered under pressure into the joint where the anchor is being implanted, the irrigations holes 16 may advantageously prevent irrigation fluid from exiting out of the proximal end 12p of the handle 12.

Figure 1C:
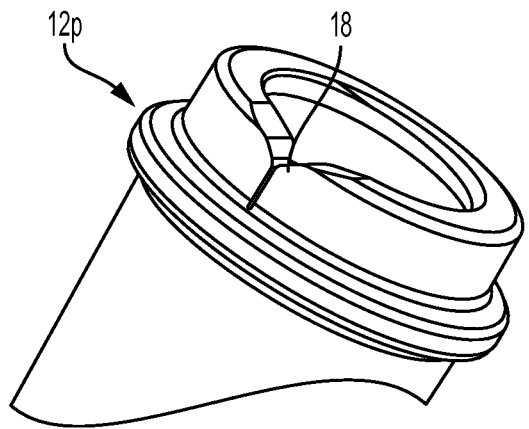
FIG. 1C is a perspective view of a proximal end of the handle of the device of FIG. 1A, showing a suture-engaging feature.
Figure 2A:
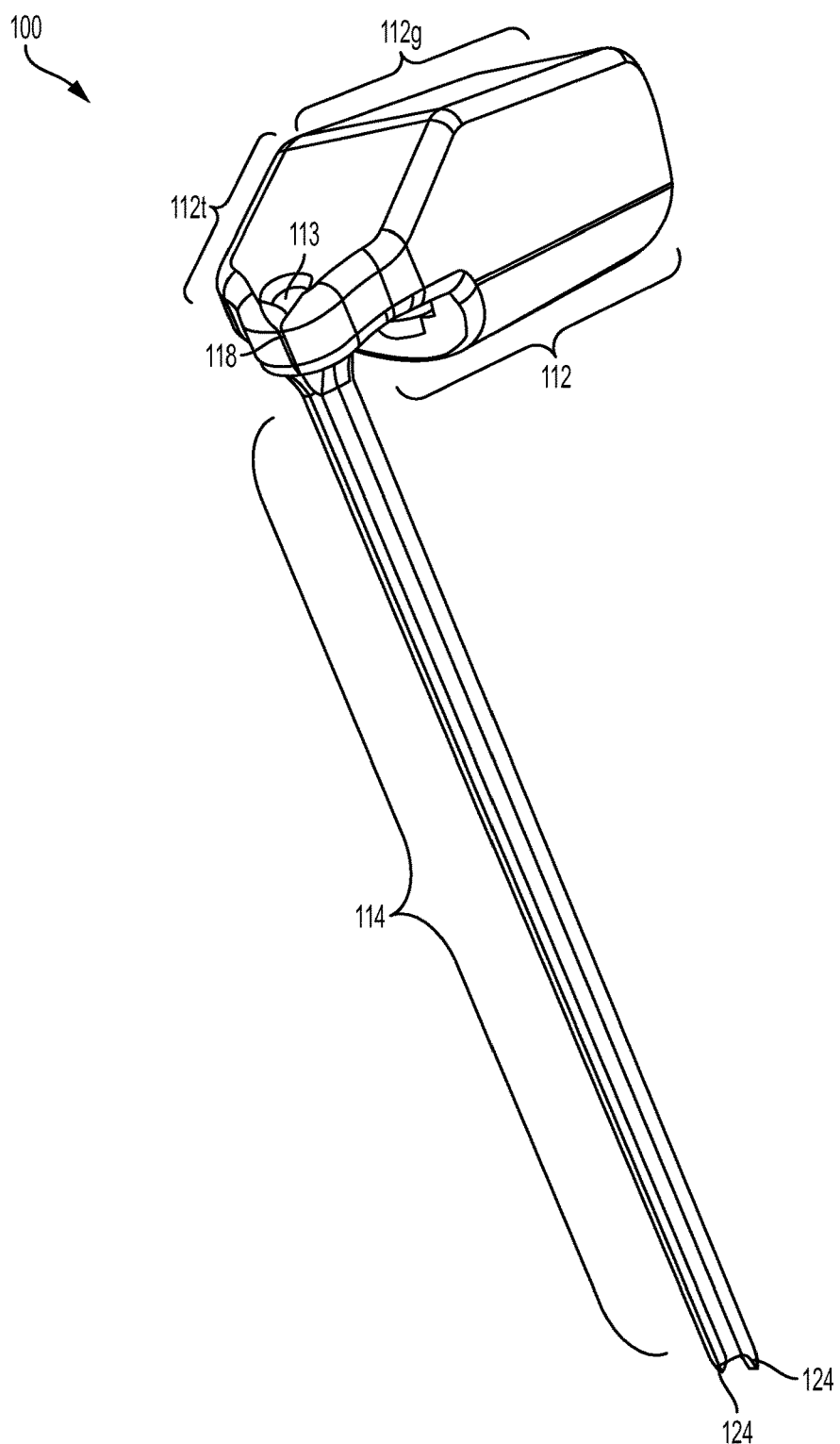
FIG. 2A is a perspective view of another embodiment of a guide device having a handle and an elongate shaft that extends at a non-zero angle relative to the handle.
Figure 2B:
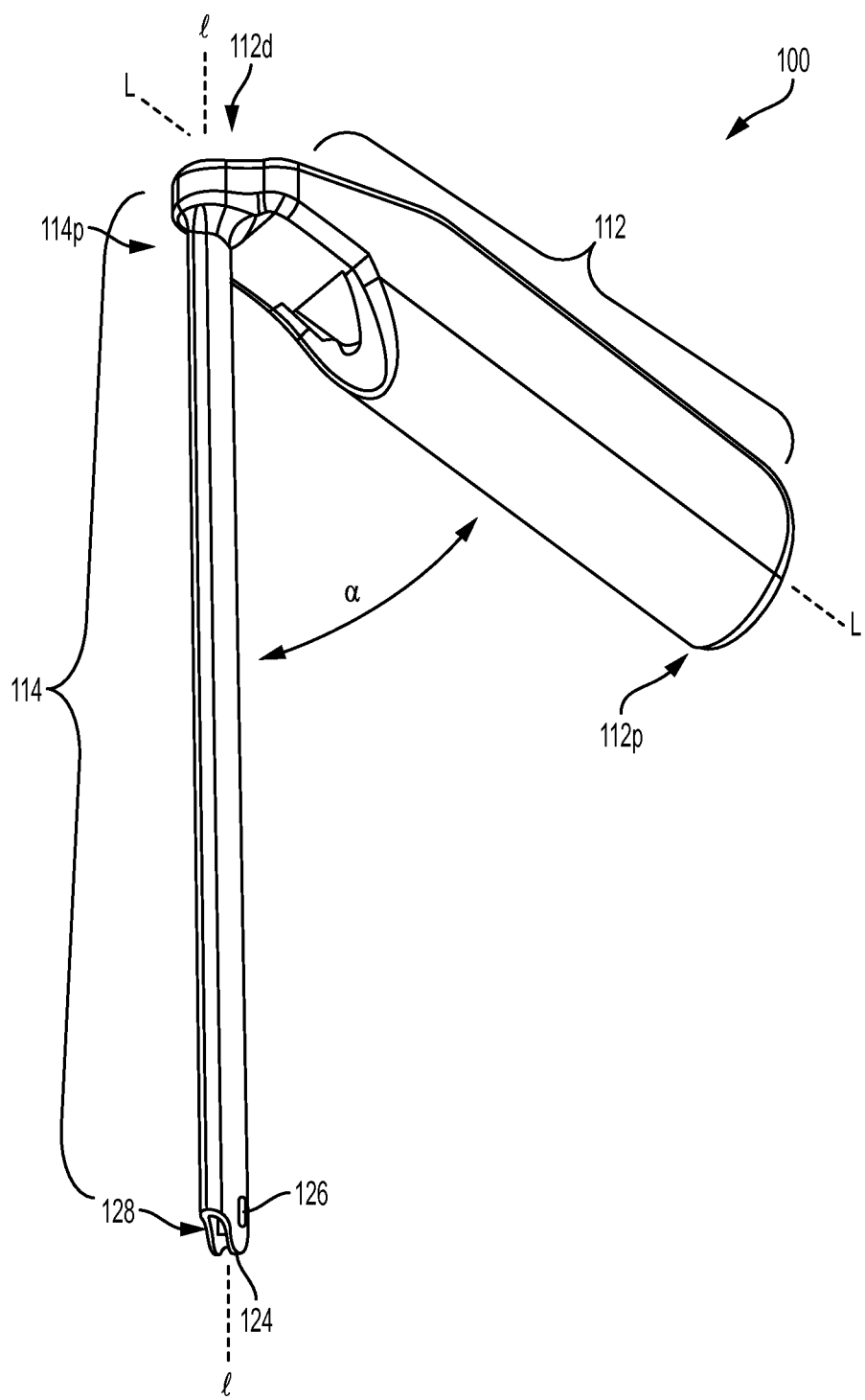
FIG. 2B is another perspective view of the device of FIG. 2A.
Figure 2C:
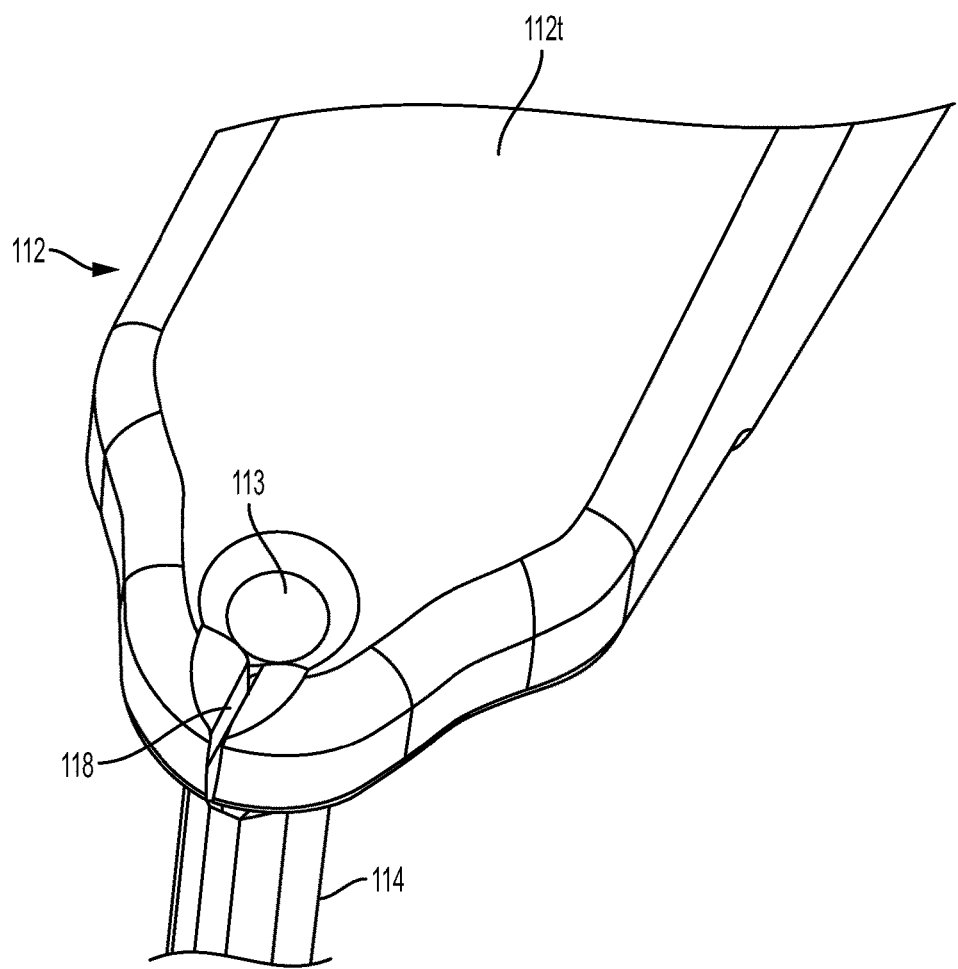
FIG. 2C is a top perspective view of the handle of the device of FIG. 2A.

As shown in FIG. 1C, the handle 12 also includes a suture-engaging feature 18 that is configured to releasably engage a suture. In the illustrated embodiment, the suture-engaging feature 18 is in the form of a slit or cleat formed in a proximal facing surface of the proximal end 12p of the handle. The illustrated suture-engaging feature 18 is on the same side as and aligned with the secondary region of the shaft. This alignment may help maintain the suture at a distance apart from a drill bit passed through the inner lumen of the shaft, and may thus prevent the cutting portion of the drill bit from causing damage to the suture. The illustrated slit has an enlarged mouth with sloping sidewalls that merge toward the slit. This may facilitate insertion of a suture into the slit. In one embodiment, the slit has a width that allows two strands of suture legs to slide therein and to be fixedly and non-slidably maintained. The suture-engaging feature can thus allow tension to be maintained on a suture extending through shaft 14 and the handle 12.

Figure 4:
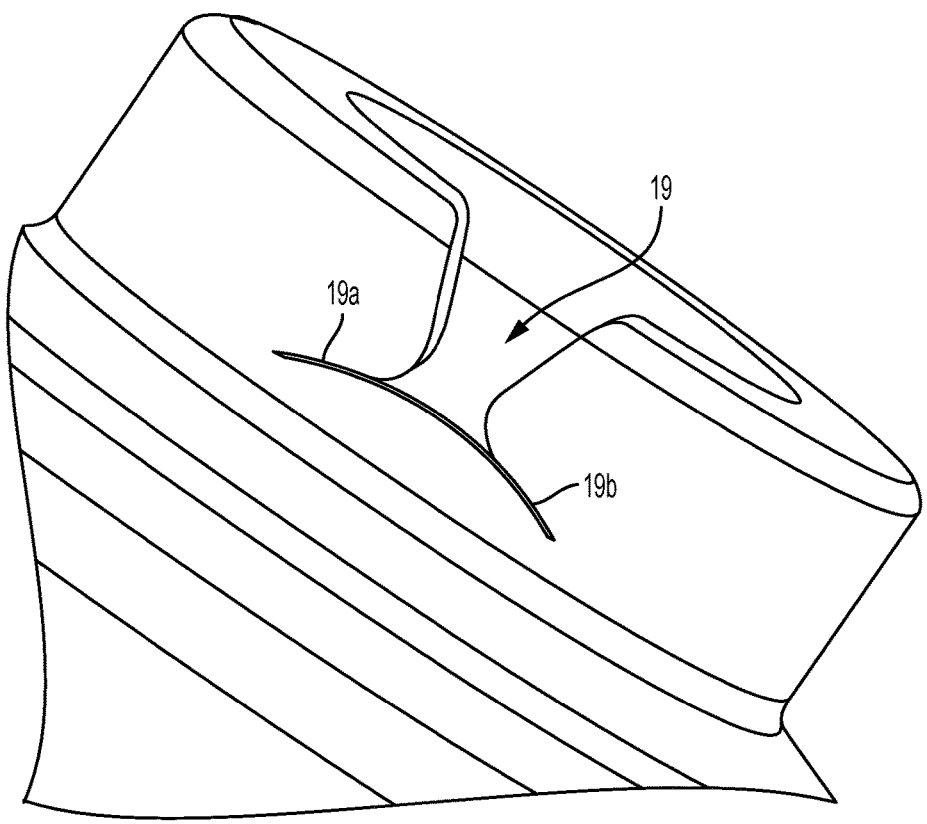
FIG. 4 is a side perspective view of another embodiment of a suture-engaging feature.

The suture-engaging feature can have a variety of other configurations. By way of non-limiting example only, FIG. 4 illustrates another embodiment of a suture-engaging feature 19 having an enlarged mouth both with two opposed slits 19a, 19b extending outward from opposite sides of the mouth. This configuration can allow a first suture leg to be positioned in one of the slits 19a while a second suture leg is positioned in the other slit 19b.

A person skilled in the art will appreciate that the suture-engaging feature can have a variety of other configurations, and need not be in the form of slits. The suture-engaging feature can also be positioned at various other locations on the handle or on the shaft and is not limited to being located on the proximal end of the handle as shown.

As indicated above, the guide device 10 further includes an elongate shaft 14 having a proximal end 14p that is mated to a distal end 12d of the handle 12, and having a distal end 14d that is configured to be positioned adjacent to an anchor site on bone. The shaft 14 can have various shapes and sizes, but in one embodiment that shaft is configured such that the cross-sectional shape allows both a suture and a drill bit to be passed through the shaft without the drill bit causing any damage to the suture.

In an exemplary embodiment, the shaft 14 has an inner lumen with an irregular cross-sectional shape such that the shape has a primary region for receiving a drill bit and a secondary offset region for seating the suture. For example, where a circular drill bit is used, the primary region has a generally circular configuration. The secondary offset region is positioned just outside of the primary region so as to define an area extending outside of the diameter where the drill bit is passed through for seating a suture.

Figure 1D:
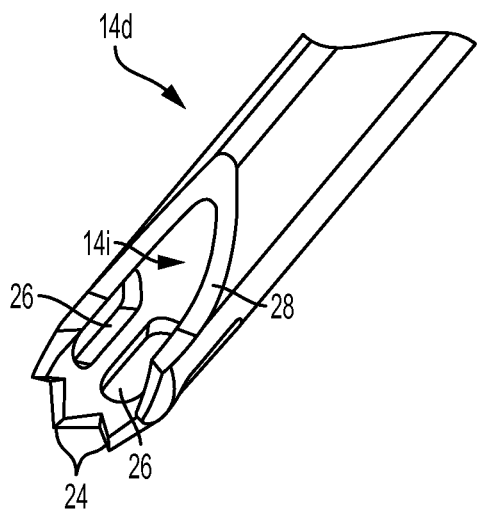
FIG. 1D is a perspective view of a distal end of the shaft of the device of FIG. 1A, showing a relief cut-out, bone engaging teeth, and viewing windows.
Figure 1E:
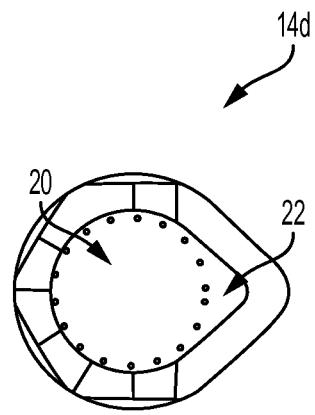
FIG. 1E is a side view of the relief cut-out formed in the distal end of the elongate shaft of FIG. 1D.

In the illustrated embodiment, as shown in FIGS. 1D and 1E, the shaft 14 has an inner lumen 14i with a primary region 20 that is generally circular and that has a diameter sufficient to allow a drill bit to pass therethrough. A secondary region 22 is offset from the primary region 20 so as to define a channel extending along the entire length of the inner lumen where the suture will reside without interference from the drill bit. The illustrated secondary region 22 has a generally triangular shape with one rounded corner for seating the suture. The cross-sectional shape of the inner lumen 14i allows the suture to move outside of the perimeter of the drill bit pathway.

Figure 5B:
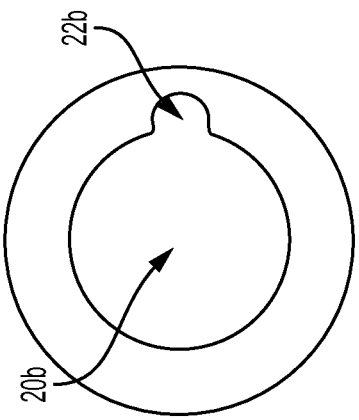
FIG. 5B is a cross-sectional view of another embodiment of an elongate shaft having a primary circular portion and an offset portion that is substantially circular.
Figure 5A:
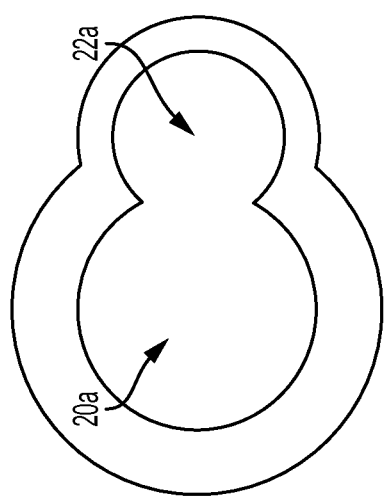
FIG. 5A is a cross-sectional view of one embodiment of an elongate shaft having a primary circular portion and an offset portion that is substantially triangular.

A person skilled in the art will appreciate that the inner lumen can have a variety of shapes and sizes as long as the suture can extend along the length of the inner lumen without coming into contact with a drill bit being passed through the inner lumen. By way of non-limiting example, FIGS. 5A and 5B illustrate additional cross-sectional configurations for a shaft of a guide device. In the embodiment shown in FIG. 5A, the primary region 20a has a substantially circular shape for receiving a drill bit, and the secondary region 22a also has a substantially circular shape however with a much smaller diameter for seating the suture. In the embodiment shown in FIG. 5B, the primary region 20b has a substantially circular shape for receiving a drill bit, and the secondary region 22b has a substantially semi-circular shape for seating the suture.

A person skilled in the art will appreciate that the shape of the primary region 20b can be configured to correspond to the shape of a drill bit, and that the second region can have any shape, such as square, rectangular, etc., as long as a suture can be positioned offset from the primary region 20b. The inner lumen can also include any number of secondary regions positioned at various locations around the perimeter thereof and extending along the length of the shaft so as to seat any number of lengths of suture.

Turning back to FIGS. 1A-1E, the distal end 14d of the shaft 14 can also have a variety of configurations. In the illustrated embodiment, the distal end 14d includes bone engaging surface features, such as one or more teeth 24, for engaging bone to prevent movement of the guide device relative to the bone. The teeth 24 are formed on the distal-facing end of the shaft 14 so as to engage or penetrate into bone when the shaft 14 is moved into contact with a bone surface. The distal end 14d also includes several viewing windows 26 formed therein to allow viewing through a sidewall of the shaft 14 into the inner lumen 14i. In the illustrated embodiment, the shaft has three viewing windows 26 spaced radially around one side of the shaft 14, and each viewing window has a generally oblong or oval shape oriented lengthwise along a longitudinal axis of the shaft. A person skilled in the art will appreciate that the shaft 14 can include any number of viewing windows at any location and having any shape.

As further shown in FIG. 1D, the shaft 14 can include a feature formed in the distal end for receiving the suture and for allowing the suture to be positioned a distance from the bone surface. In the illustrated embodiment, the feature is in the form of a relief cut-out 28 that extends from the distal end 14d of the shaft 14 and that extends proximally along a portion of one side of the shaft 14. While the position of the relief cut-out 28 can vary, in the illustrated embodiment the relief cut-out 28 is aligned with the secondary region 22 of the inner lumen 14i, such that the suture can be positioned within the relief cut-out 28 and extends along the secondary offset region 22, out of the path of a drill bit inserted through the shaft 14. The relief cut-out 28 is thus also aligned with the suture-engaging feature 18. The alignment between the relief cut-out 28 and the suture-engaging feature 18 may help maintain the suture within the offset region 22, and thus may prevent the suture from moving into the primary region 20b and into contact with any cutting portion of a drill bit passed therethrough.

The size of the relief cut-out 28 can also vary, but in one embodiment the relief cut-out 28 has a size that allows the suture to be positioned a distance from the distal-most end of the shaft 14, i.e., a distance from the bone surface. The illustrated relief cut-out 28 extends proximally beyond the viewing windows 26 so as to allow the suture to be position proximal of the viewing windows 26. Such a configuration will allow the suture to be pulled up and away from the bone so as to avoid an interference with the drill bit, and to allow viewing of the bone and drill bit tip without interference from the suture.

The shape of the relief cut-out 28 can vary. As shown in FIG. 1D, the relief cut-out is substantially U-shaped with curved or concave sidewalls. The relief cut-out can have a variety of other shapes. By way of non-limiting example, FIGS. 6A-6C illustrate additional embodiments of relief cut-outs that can be used on any of the guide devices disclosed herein.

Figure 6B:
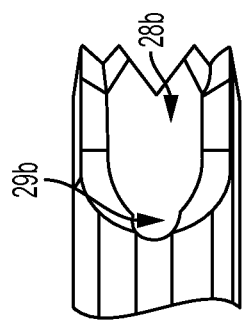
FIG. 6B is a side view of yet another embodiment of a relief cut-out formed in a distal end of an elongate shaft.
Figure 6C:
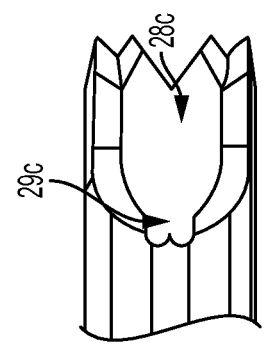
FIG. 6A is a side view of another embodiment of a relief cut-out formed in a distal end of an elongate shaft.
FIG. 6 C is a side view of yet another embodiment of a relief cut-out formed in a distal end of an elongate shaft.
Figure 6A:
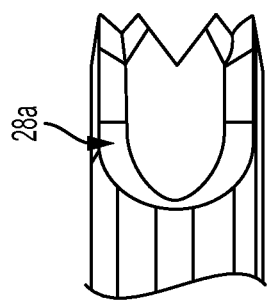

As shown in FIG. 6A, the relief cut-out 28a is similar to the relief cut-out 28 shown in FIG. 1D, and has a substantially semi-circular or U-shape.

In FIG. 6B, the relief cut-out 28b is U-shaped, but it includes an additional cut-out or notch 29b formed therein. The notch 29b is in the form of a small semi-circular feature that is configured to seat the suture to help prevent sliding of the suture.

In FIG. 6C, the relief cut-out 28c is also U-shaped, but in this embodiment it includes two notches 29c formed therein. A first leg of suture can be seated in one of the notches and a second leg of suture can be seated in the other notch. This may help align the sutures and prevent twisting of the sutures within the inner lumen 14i.

A person skilled in the art will appreciate that the relief cut-out can be formed at various locations, it can have various sizes, and the shape can vary as desired.

FIGS. 2A-2C illustrate another embodiment of a guide device 100 that is similar to guide device 10, but that has a different handle configuration. Accordingly, all of the features discussed above with respect to guide device 10 can be included in guide device 100. As shown, guide device 100 has a handle 112 and an elongate shaft 114 coupled to and extending from the handle 112. The shaft 114 has the same configuration as shaft 14 discussed above, and includes a distal tip having bone-engaging teeth 124, one or more viewing windows 126, and a relief cut-out 128.

The handle 112 in this embodiment, unlike handle 12, extends at an angle relative to the elongate shaft 114. In particular, the handle 112 has a generally elongate configuration defining a longitudinal axis L with proximal and distal ends 112p, 112d. The distal end 112d is coupled to the shaft 114 such that a longitudinal axis 1 of the shaft 114 extends at a non-zero angle relative to the longitudinal axis of the handle 112. In the illustrated embodiment, the angle α between the handle's longitudinal axis L and the shaft's longitudinal axis 1 is equal to or less than 90 degrees. In order to form such an angle, the proximal end 114p of the shaft 114 can be coupled to a side surface of the handle, rather than extending from the distal end.

In the illustrated embodiment, the handle 112 has a grasping portion 112g that is substantially cylindrical with various flattened sides, and a tip portion 112t formed at the distal end 112d that the shaft 114 is mated to. The illustrated tip portion 112t has a tapering or inclined configuration, where a top surface is angled relative to a top surface of the grasping portion 112g to form a more pointed tip on the tip portion 112t. The distal region of the tip portion 112t includes a bore 113 formed therein for mating the shaft 114 to the tip portion 112t. The bore 113 is co-axial with and in communication with the lumen in the shaft 114.

In use, the angular orientation of the handle 112 relative to the shaft 114 may facilitate manipulation of the guide device 100, especially in joints such as the hip that can be difficult to access. A person skilled in the art will appreciate that the handle can have a variety of shapes and sizes and that it can be positioned at various angles relative to the shaft as may be desired based on the intended use.

In one embodiment, the entire tip portion 112t, portions of the tip portion 112t, and/or the shaft 114 can be movably and/or detachably coupled to the remainder of the handle 112. Such a configuration may, for example, allow the grasping portion 112g of the handle to be rotated and positioned as desired relative to the shaft 114. A locking feature can be provided for locking the handle 112 in a desired orientation relative to the shaft 114.

As further shown in FIGS. 2A and 2C, the tip portion 112t includes a suture-engaging feature 118 formed therein that is similar to suture-engaging feature 18. In particular, the suture-engaging feature 118 is in the form of a slit or cleat formed in the tip portion 112t for allowing a suture extending out of the inner lumen of the shaft 114 to be positioned therein and to be releasably retained. A person skilled in the art will appreciate that the suture-engaging feature 118 can be formed at various locations on the shaft 114 and/or on the handle 112, and that it can have a variety of shapes and sizes as discussed above.

FIGS. 3A-3B illustrate another embodiment of a guide device 200 having a handle 212 and an elongate shaft 214 that are similar to the handle 112 and shaft 114 discussed above with respect to FIGS. 2A-2C. In this embodiment, however, the handle 212 includes a support arm 213 mated thereto. In particular, a tip portion 212t of the handle 212 includes an extension rod 215 coupled thereto and extending laterally outward therefrom in a direction substantially perpendicular to the shaft 214. The support arm 213 is mated to an end of the extension rod 215 and extends substantially parallel to the handle 212. The support arm 213 can be slightly angled away from the handle 212 toward a proximal end of the device as may be desired. The support arm is 213 can have a generally elongate shape with an elongate substantially c-shaped channel 213c formed therein along the length thereof. The channel 213c can be configured to seat a tool, such as an inserter tool for inserting an anchor through the shaft 214.

The support arm 213 can also include support features 213s, such as opposed tabs extending upward from opposed sides of the channel 213c to help support and retain a shaft of an inserter tool within the support arm 213.

A person skilled in the art will appreciate that the support arm 213 can be used in connection with any of the guide devices disclosed herein, and that it can have a variety of configurations for retaining an inserter tool. For example, the support arm can vary in length, and it can have a length that is shorter than a length of the guide device. The support arm can additionally or alternatively be detachable, and it can be formed on or removably matable to either side or both sides of the drill guide.

In use, an anchor coupled to a suture extending proximally out of the shaft can be mounted onto a distal tip of a tool, and the tool can be seated within the support arm 213 or within any feature on the support arm while a drill bit is passed through the shaft to form a bone hole in the bone. Once the bone hole is formed, the tool can be removed from the support arm 213, and the tool with the anchor on the tip can be passed through the shaft. The suture can remain in engagement with the suture-engaging feature so as to provide tension to the suture while the anchor is passed through the shaft. This may free up a user's hand during the procedure.

Various methods for reattaching soft tissue to bone are also provided herein. In general, a suture is coupled to tissue to be reattached, and an anchor having the suture coupled thereto is implanted in a bone hole at an attachment location. The suture is tensioned to pull the tissue toward the bone. The anchor can be configured to lock and prevent sliding of the suture, thereby reattaching the tissue to the bone.

Figure 7:
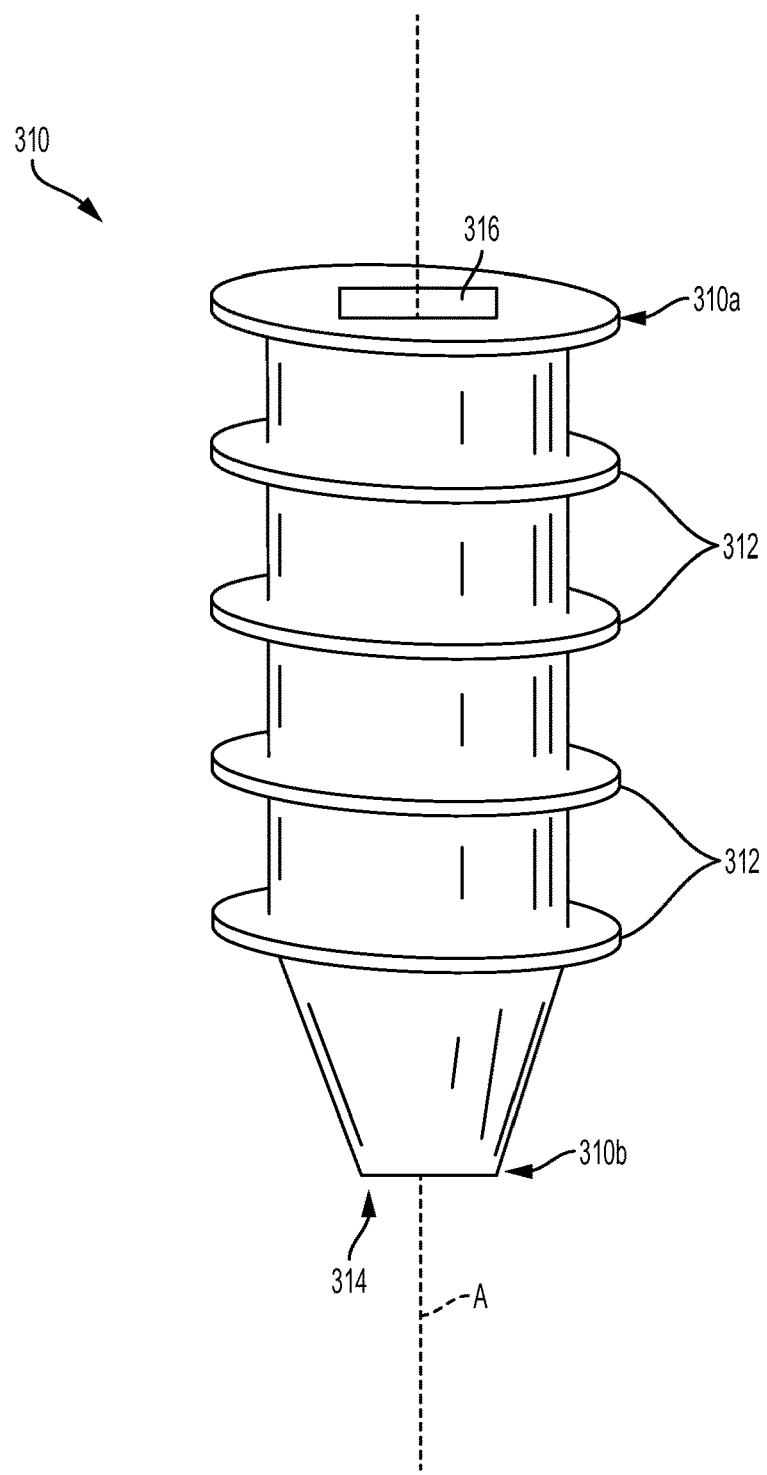
FIG. 7 is a side view of one embodiment of a suture anchor.

Suture anchors having a variety of different constructions can be used with the methods disclosed herein. By way of example, FIG. 7 illustrates one embodiment of a suture anchor 310. As shown, the suture anchor 310 is generally elongate with a longitudinal axis A extending between a proximal end 310a and a distal end 310b. The suture anchor 310 can also have at least one feature, such as threads 312, configured to engage bone. The suture anchor 310 can also have features for receiving a suture therein. By way of non-limiting example, the suture anchor 310 of FIG. 7 has an inner lumen 314 that extends between proximal and distal ends 310a, 310b, along a longitudinal axis A of the suture anchor 310, for receiving a suture. In another embodiment, an aperture (not shown) can extend at least partially through the suture anchor 310 along an axis transverse to longitudinal axis A. As will also be appreciated by a person skilled in the art, the suture anchor can alternatively have one or more apertures or openings disposed at any location on the anchor, such as on a sidewall of the anchor. Such apertures can form a pathway for receiving a suture that can be curved, or of any other shape. The suture anchor 310 can also be a knotless suture anchor that allows a user to thread the anchor with suture and form a loop without tying a knot. By way of non-limiting example, a suture (not shown) can be threaded through the anchor by inserting one terminal end of the suture through the proximal end 310a of the anchor, passing it distally, moving around a distal end 310b of the suture anchor, and out through a sidewall of the anchor. A suture threader (not shown) can also be used to thread the suture through suture anchor 310. The suture anchor 310 can also have a mating feature 316 positioned on the proximal end 310a of the anchor and configured to mate with a distal end of an inserter tool. A person skilled in the art will appreciate that various suture anchors known in the art can be used in connection with the guide devices and methods disclosed herein.

In use, the procedure usually begins by preparing the patient for surgery and making one or more appropriately sized incisions at a desired location. In a minimally invasive procedure, one or more cannulas (not shown) can be positioned in the incisions to provide access to the surgical site. One skilled in the art will also understand that one or more viewing devices, e.g., scopes, can be placed in one of the incisions to allow medical personnel to view the surgical site from outside the body.

Figure 8A:
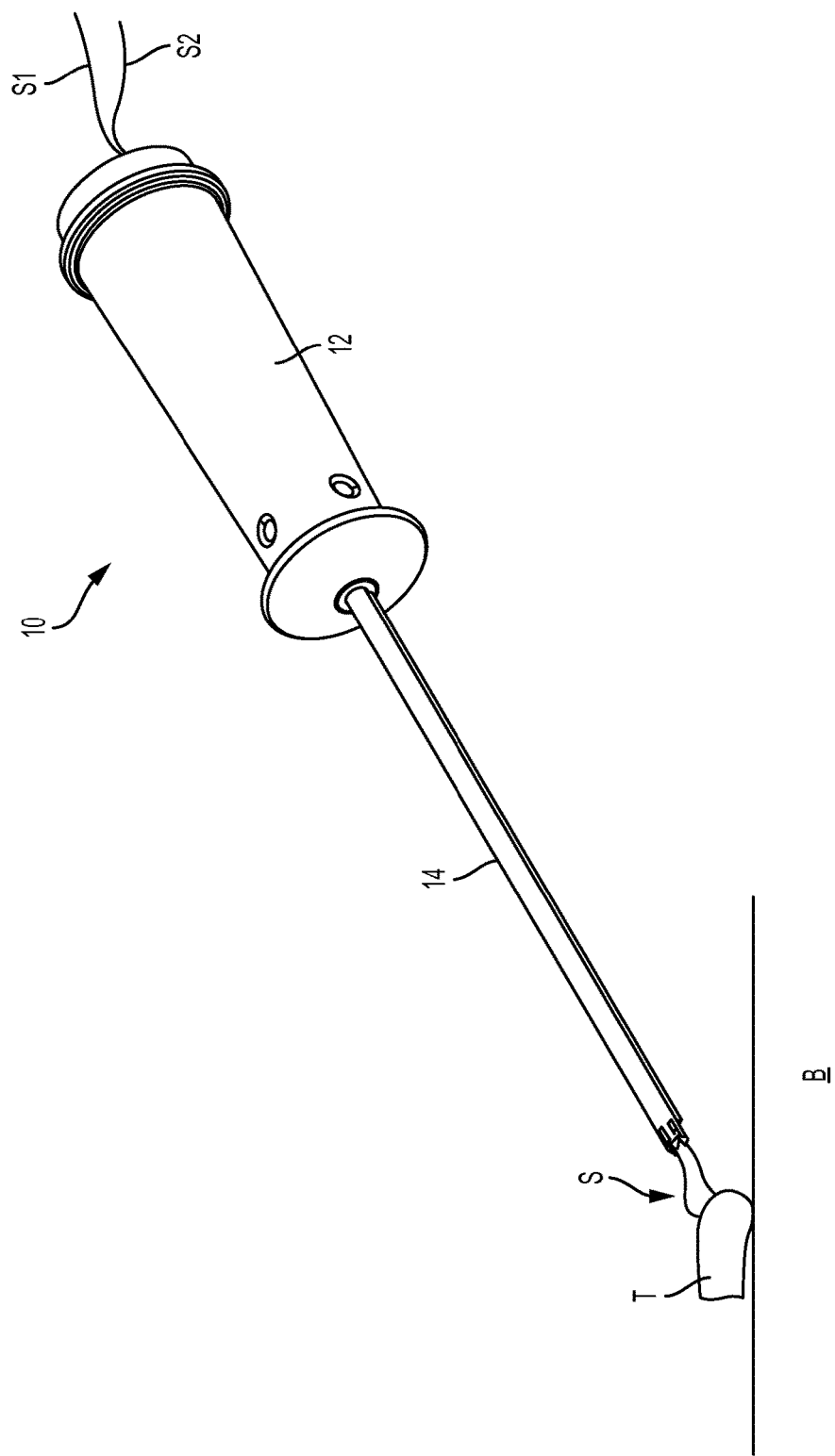
FIG. 8A is a perspective view of the guide device of FIG. 1A shown with a suture extending therethrough and coupling to tissue.

Once the patient is prepared for surgery, a length of suture S is passed into the patient's body and passed through soft tissue T that is to be surgically reattached to bone B. As shown in FIG. 8A, the suture S can be passed through tissue T such that the terminal ends S1, S2 are positioned outside of the patient's body. One skilled in the art will appreciate that the suture can be passed through the tissue using any known surgical technique, such as by mattress and cinch loop methods. With the suture so positioned, a guide device (e.g., guide device 10 is shown by way of example) is positioned within the surgical site with the suture S being positioned within the lumen in the shaft 14 of the guide device 10. This can be accomplished by a variety of known techniques, including by passing a suture passer (not shown) into the lumen of the shaft 14 and out of the proximal opening in the handle 12 such that the two limbs S1, S2 of the suture S extend out of the handle 12.

Once the suture S is positioned through the guide device 10, the suture limbs S1, S2 extending from the handle 12 can be tensioned so as to cause the suture to sit within the relief cut-out in the distal end of the shaft 14, and to be seated in the secondary offset region along the entire length of the shaft 14. The limbs S1, S2 extending out of the handle 12 can be passed into the suture-engaging feature (not shown) formed on the handle 12 of guide device 10, which will maintain and prevent sliding of the suture S. In an exemplary embodiment, the relief cut-out, the secondary region, and the suture-engaging feature are all longitudinally aligned and are all positioned at the same radial location around the perimeter of the shaft 14 so as to maintain the suture off to one side of the shaft 14.

Figure 8B:
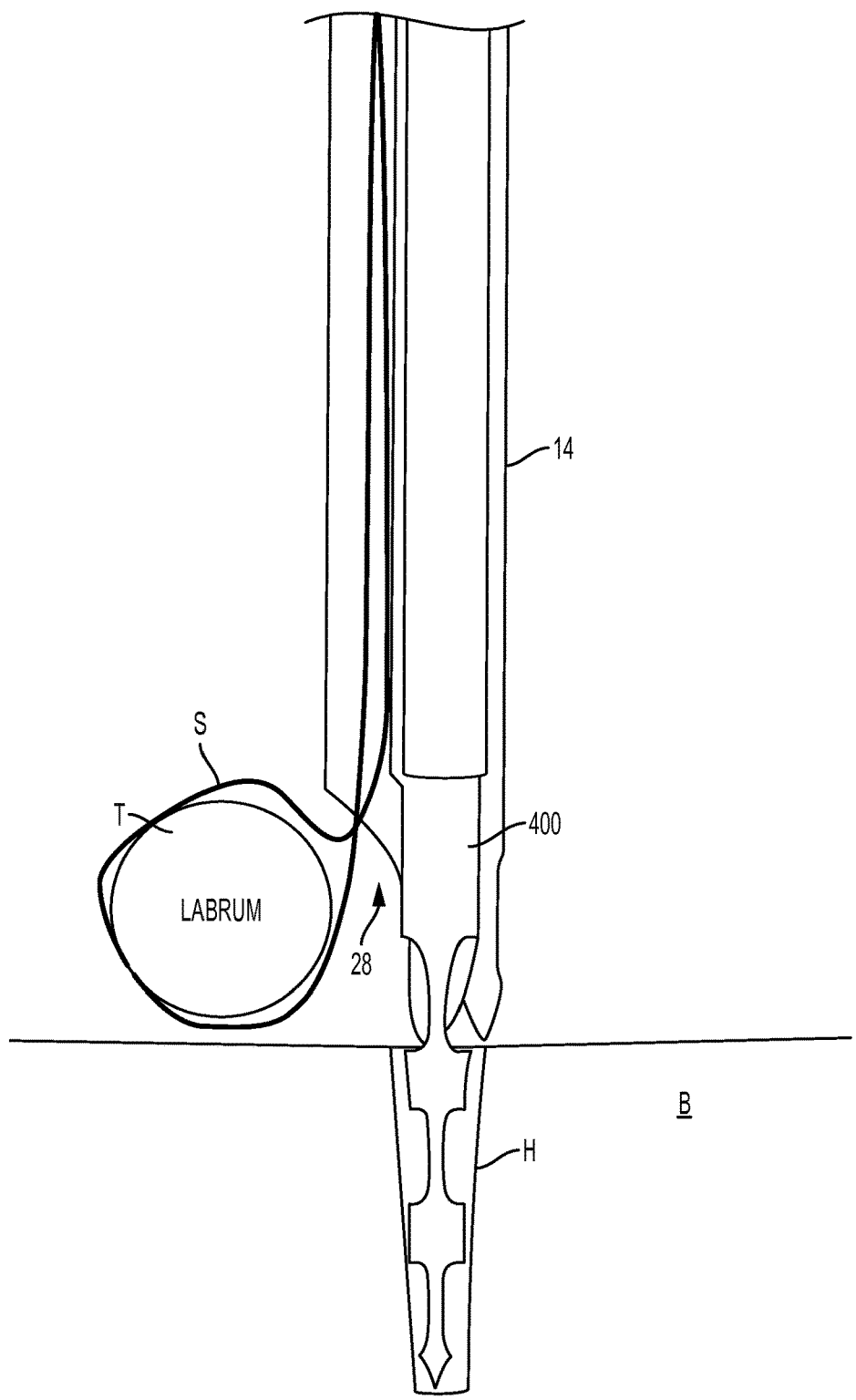
FIG. 8B is a side view of a distal end of the guide device, suture, and tissue of FIG. 8A.

With the suture seated in the secondary offset region of the shaft, the bone engaging teeth on the distal end of the shaft 14 on the guide device 10 can be positioned to abut bone B, as shown in FIG. 8B. The shaft 14 should be oriented such that the relief cut-out 28 faces the tissue T being reattached. As so positioned, the suture adjacent to the distal end of the shaft 14 will extend across the relief cut-out 28 toward the tissue. The suture S will thus be pulled up and out of the way of the bone surface. If the relief cut-out includes two notches formed therein, each limb of suture can be seated in a notch so as to prevent twisting of stacking of the suture S as it extends through the inner lumen. A drill bit 400 can then be passed through the shaft 14, as shown in FIG. 8B to form a hole in the bone B. The cutting tip on the drill bit can be rotated, manually or by a motor, to advance the cutting tip through bone to form a hole. During drilling, a user can grasp the handle 12 of the guide device 10 to maintain the position of the guide device 10 relative to the bone. Grasping of the suture is unnecessary since it is held by the suture-engaging feature. Since the drill bit only occupies the primary region of the shaft and the suture S is maintained in the secondary offset region, as shown in FIG. 8B, the drill bit flutes will not contact or cause damage to the suture S.

Figure 8C:
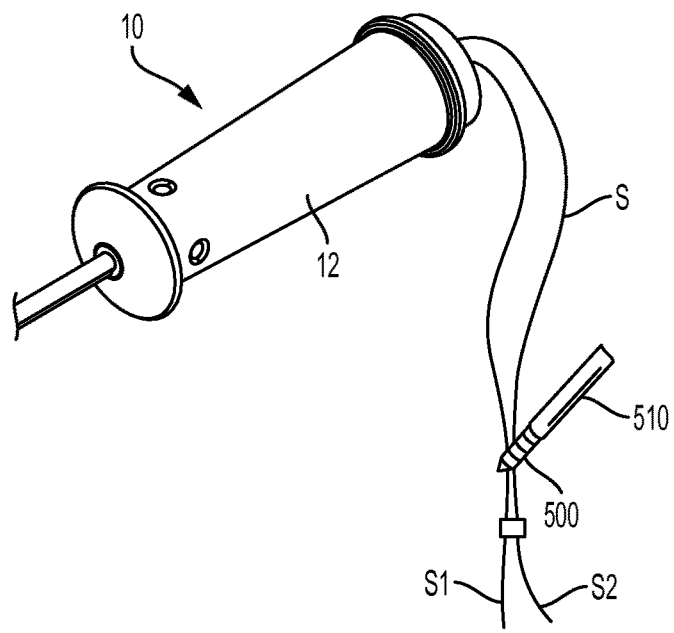
FIG. 8C is a perspective view of the guide device, suture, and tissue of FIG. 8A, showing an anchor coupled to trailing ends of the suture.

Once the bone hole is formed, the drill bit can be removed, leaving the guide device 10 in contact with the bone surface. A downward force can be applied to the guide device 10 to cause the bone engaging teeth 124 to dig into the bone surface to hold the guide device 10 in position against the bone while the drill bit is removed. After the suture S is passed through the guide device 10, and either before or after the bone hole is formed, an anchor, e.g., anchor 500 is shown, can be mated to the trailing limbs S1, S2 of the suture S. This can be achieved by threading the suture S onto the anchor 500 as known based on the configuration of the anchor. With the anchor 500 mated to the suture S, as shown in FIG. 8C, the anchor 500 can be mounted onto an inserter tool, e.g., tool 510 (only a portion of which is shown). If guide device 200 is used, the inserter tool 510 can be seated in the support arm until it is ready for use.

Figure 8D:
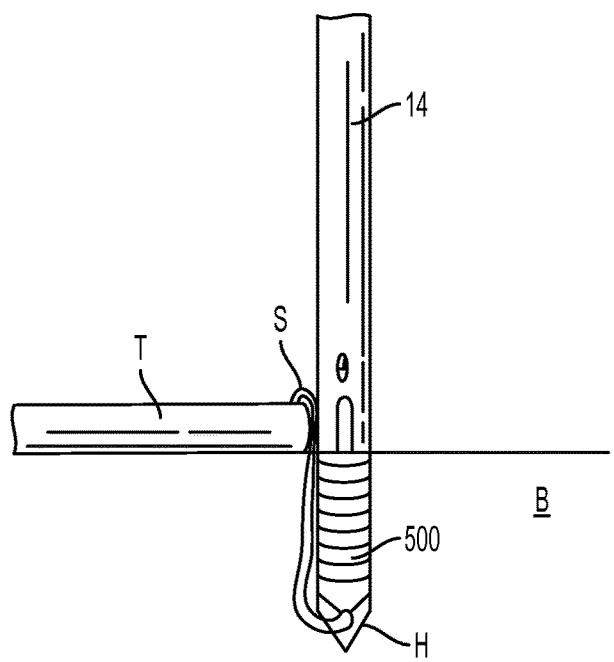
FIG. 8D is a side view of a distal portion of the guide device of FIG. 8A, showing the anchor implanted in the bone hole and the suture tension to reattach the tissue to bone.

In order to implant the anchor, the suture can be tensioned to position the tissue T at a desired location relative to the bone B, and while maintaining tension of the suture the inserter tool 510 can be manipulated to slide the anchor 500 along the suture through the guide device 10 and into the bone hole H, as shown in FIG. 8D. As the inserter tool 510 is passed through the guide device 10, the anchor 500 can slide along the suture S so that the terminal ends S1, S2 remain outside of the patient's body. Continued alignment between the shaft 14 of the guide device 10 and the bone hole as the anchor 500 is inserted ensures that a longitudinal axis of the anchor 500 is aligned with a longitudinal axis of the bone hole. Such alignment minimizes the risk of inserting the anchor at an improper angle, which may damage the bone anchor and/or cause the anchor to fail.

A user can monitor the position of the anchor 500 within the guide device 10 using a scoping device that is focused on one or more of the viewing windows in the shaft 14. The viewing windows will allow viewing of the drill bit, the suture, and the anchor. Once the anchor 500 is partially seated within the drilled hole H, the terminal ends S1, S2 of the suture S can be further pulled to tension the suture S and thereby pull the attached tissue T closer to the anchor 500, and thus, to the position of bone to which it is to be secured. The anchor 500 can be driven into the hole H, such as by rotating and/or tapping the proximal end of the inserter tool 510. This action serves to lock the suture S between an outer surface of the anchor 500 and an inner surface of the drilled hole H. As will be appreciated by a person skilled in the art, the anchor can lock the suture S in other ways, such as using a set screw or internal interference feature. After the anchor 500 is fully seated in the hole H, as shown in FIG. 8D, the guide device 10 can be removed from the surgical site and the ends of the suture S can be trimmed.

The systems and methods described above can be used for a variety of tissue attachment procedures including, by way of non-limiting example, arthroscopic shoulder surgery. For example, the suture can be passed through the labrum and the drill guide can also be used to lever the humeral head away from the glenoid cavity to gain access to the glenoid rim prior to drilling the bone. A person skilled in the art will also appreciate that the guide device can be used in connection with a guide wire instead of or in addition to a suture. The guide wire can be seated within the secondary offset region of the shaft during drilling, and the anchor can subsequently be advanced along the guidewire during insertion.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The invention described herein can be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A knotless suture anchor guide device, comprising:
a handle and a shaft extending distally from the handle, the shaft having an inner lumen that includes a primary region configured to receive a drill bit therethrough, and an offset region configured to seat a length of suture such that the suture seats outside of the primary region and thus does not come into contact with a cutting portion of the drill bit, the primary region and the offset region combined forming a non-circular cross-sectional shape of the inner lumen extending through an entire length of the shaft, and at least one of the shaft and the handle including a suture-engaging feature for engaging a suture extending through the inner lumen, and the shaft including a distal end with a relief cut-out formed therein for seating a suture extending through the inner lumen.

2. The device of claim 1, wherein the handle has a generally elongate cylindrical shape with an inner lumen extending therethrough and co-axial with the inner lumen of the shaft.

3. The device of claim 1, wherein the handle extends at a non-zero angle relative to the shaft.

4. The device of claim 1, wherein the suture-engaging feature comprises a slit for releasably engaging a suture.

5. The device of claim 1, wherein the relief cut-out and the suture-engaging feature are configured to together maintain the suture within the offset region.

6. The device of claim 1, wherein the handle includes an irrigation hole formed therein and in communication with the inner lumen of the shaft such that irrigation fluid can flow through the shaft and exit through the irrigation hole.

7. The device of claim 1, wherein the handle includes a side arm coupled thereto and having a channel configured to seat an elongate tool therein.

8. The device of claim 1, wherein the relief cut-out and the suture-engaging feature are longitudinally aligned with the offset region.

9. The device of claim 1, wherein the relief cut-out in the distal end of the shaft is substantially U-shaped and includes at least one notch formed in a proximal end thereof.

10. The device of claim 1, wherein the offset region of the elongate shaft is substantially triangular.

11. The device of claim 1, wherein the offset region of the elongate shaft is substantially circular.

12. The device of claim 1, wherein the offset region of the elongate shaft is substantially semi-circular.

13. A suture anchor and delivery kit, comprising
a delivery tool having a handle with an elongate shaft extending distally therefrom, the shaft having an inner lumen extending therethrough, the inner lumen having a primary region for receiving a drill bit and a secondary offset region, the primary region and the secondary offset region combined forming a non-circular cross-sectional shape of the inner lumen extending through an entire length of the shaft; and
a suture anchor assembly having
an anchor configured to be implanted in bone, and
a suture configured to be coupled to the anchor;
wherein the suture is configured to extend through the inner lumen in the shaft and to sit within the secondary offset region such that a drill bit can be passed through the primary region of the inner lumen in the shaft without contacting the suture.

14. The kit of claim 13, wherein the handle has an inner lumen extending therethrough and in communication with the inner lumen in the shaft.

15. The kit of claim 13, wherein the delivery tool includes a suture-engaging feature configured to releasably engage the suture.

16. The kit of claim 13, wherein a distal end of the shaft includes a relief cut-out formed therein and longitudinally aligned with the secondary offset region of the inner lumen.

17. The kit of claim 13, wherein a distal end of the shaft includes a viewing window formed therein.

18. The kit of claim 13, wherein a distal end of the shaft includes bone engaging teeth formed thereon.

19. The kit of claim 13, wherein the handle includes an irrigation hole formed therein and configured to allow irrigation fluid to flow through the inner lumen in the shaft and to exit through the irrigation hole.

* * * * *